United States Patent [19]

Miller

[11] Patent Number: 4,991,104

[45] Date of Patent: Feb. 5, 1991

[54] COMPUTER GENERATED STOPPER

[75] Inventor: Henry F. Miller, Clifton, N.J.

[73] Assignee: Becton, Dickinson and Company, Franklin Lakes, N.J.

[21] Appl. No.: 496,111

[22] Filed: Mar. 19, 1990

Related U.S. Application Data

[60] Continuation of Ser. No. 320,915, Mar. 7, 1989, abandoned, which is a continuation of Ser. No. 155,432, Feb. 12, 1988, abandoned, which is a division of Ser. No. 947,311, Dec. 29, 1986, Pat. No. 4,741,446.

[51] Int. Cl.$^5$ .................... G06F 15/46; B65D 47/36
[52] U.S. Cl. .................. 364/476; 215/247; 364/149; 364/473
[58] Field of Search ........ 364/468, 473, 476, 148–151, 364/191, 496, 500; 215/247–249, 260, 270, 355, DIG. 3; 604/415; 264/40.1–40.7; 425/135, 140, 141, 149, 162, 163

[56] References Cited

U.S. PATENT DOCUMENTS

| | | | |
|---|---|---|---|
| 1,509,916 | 9/1924 | Waite | 215/247 |
| 3,136,440 | 6/1964 | Krug et al. | 215/247 |
| 3,974,930 | 8/1976 | Gizard et al. | 215/247 |
| 4,111,326 | 9/1978 | Percarpio | 215/247 |
| 4,136,794 | 1/1979 | Percarpio | 215/247 |
| 4,186,840 | 2/1980 | Percarpio | 215/247 |
| 4,187,952 | 2/1980 | Percarpio | 215/247 |
| 4,301,936 | 11/1981 | Percarpio | 215/247 |
| 4,465,200 | 8/1984 | Percarpio | 215/247 |
| 4,473,215 | 9/1984 | Rathfon, II et al. | 364/476 |
| 4,546,438 | 10/1985 | Prewitt et al. | 364/473 |
| 4,641,270 | 2/1987 | Lalloz et al. | 364/476 |

OTHER PUBLICATIONS

Algor Newsletter, Jul. 1988, "Redesigning Skyscraper Facades Using Finite Element and Wind Tunnel Analysis Techniques".
Algor Design World, Apr. 1989, "FMC and Algo-b—Ten Year Partners in FEA".
Algor Newsletter, May, 1988, "PC-Based Finite Element Analysis Reveals Dangerously Low Resonance in Coastal Tower".
Algor Newsletter, Apr., 1988, "Analysis of the Structure of the Keck Telescope".
Algor Newsletter, Jan. 1988, "PC-Based Finite Element Analysis Helps Sell Crane Assembly Design".
Algor Newsletter, Oct., 1987, "PC-Based Finite Element Analysis Proves Out Oil Production Platform's Riser Tension System".
Algor Newsletter, Nov., 1987, "Turbine Design Optimized in Just Four Days Using Algor Finite Element Analysis on a PC".
Mechanical Engineering, Jul., 1986, "Finite Elements on the PC: No Excuses Left".

Primary Examiner—Joseph Ruggiero
Attorney, Agent, or Firm—Robert P. Grindle

[57] ABSTRACT

A stopper or closure is provided as a closure for containers in which the stopper profile is computer generated to take into consideration radial stress at the stopper/container interface, and to eliminate tensile stress therealong which tensile stress is an indication that a portion of the stopper wall is not engaging the opposed container surface. The stopper of the invention is particularly appropriate for use in evacuated blood sample collection tubes for eliminating "gray bands" or regions where the stopper and tube do not contact, and "red spots" formed in small cavities generated on the internal surface of the stopper at the withdrawal position of a blood collection needle having been inserted in the stopper.

3 Claims, 4 Drawing Sheets

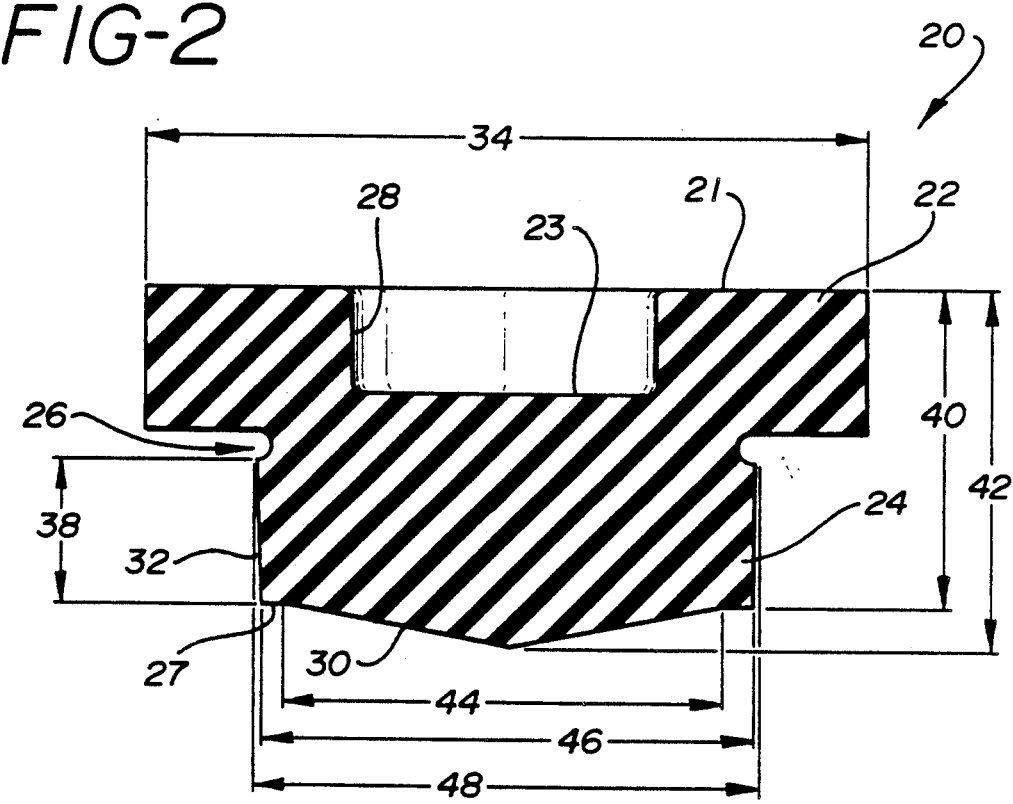
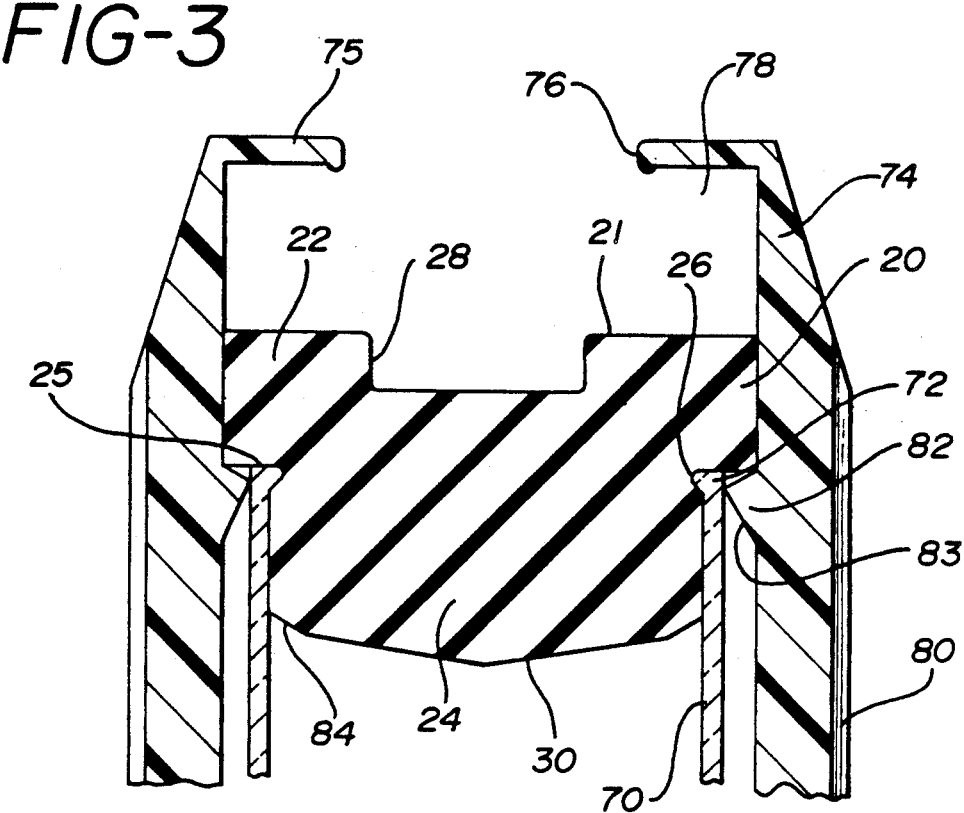

COMPUTER GENERATED STOPPER

This application is a continuation of Ser. No. 07/320,915 filed Mar. 7, 1989, abandoned, which is a continuation of Ser. No. 07/155,432 filed Feb. 12, 1987, abandoned which is a division of Ser. No. 06/947,311, U.S. Pat. No. 4,741,446, filed Dec. 29, 1986.

BACKGROUND AND DESCRIPTION OF THE INVENTION

This invention relates generally to a closure assembly for containers and more particularly to such assemblies for use with evacuated blood collection tubes such as VACUTAINER ® Brand evacuated tubes. More particularly, this invention relates to such a closure assembly and the deliberate profile formation of the rubber or elastomer stopper portion of the assembly generated from a computer readout in order to eliminate tensile stress along the stopper/ container wall interface so as to more clearly define and seal the container with the stopper. The computer generated stopper of the invention is so configured that the forces generated by the insertion of the stopper into the container are utilized in order to improve and develop continuous compressive radial stresses along the entire stopper/container interface.

As is well known in the medical field, both evacuated and non-evacuated tubes are used in large quantities to take blood samples from patients for subsequent testing of the blood for various purposes to determine if a patient has certain diseases or blood problems or other physical health problems of some kind. It is routine for a laboratory technician, for example, to take several such samples from a single tube for various tests. Since the tube may be evacuated, there is a pressure differential across the stopper holding the sample in the tube. Thus, when a needle is inserted through the diaphragm of the stopper, there can be an aerosol of the sample which may spray onto the technician. Moreover, when taking samples, sometimes blood droplets are left on the top and bottom surface of the stopper during the removal of the needle once the sample has been taken from the evacuated tube which creates a contamination problem for anyone handling the stopper subsequently.

A further problem with the use of stoppers of the kind discussed above, is the fact that an improper seal is generated along the stopper/container surface interface. The seal is discontinuous merely because of the stresses generated by the configuration of the stopper itself, and its interaction with the container involved. Such problems have the effect of reducing the shelf-life of evacuated tubes and are referred to by practitioners-in-the-art as "gray band" regions because they look gray when looking at the stopper through a transparent container wall. When one realizes the vast number of such tubes required for daily taking of blood samples in many many hospitals, it becomes important to reduce the cost of such items by increasing the shelf-life thereof. If a vacuum can be maintained at a proper level for a longer period, it follows that the evacuated tubes will have a much longer shelf-life and be in a better condition for use when required.

Attempts have been made in the past to overcome some or all of the above-noted problems. For example, U.S. Pat. No. 3,974,930 to Gizard et al. teaches a stopper with a central hole in the top surface of the diaphragm for protecting personnel from blood droplets on the outside surface of the stopper diaphragm. However, the Gizard et al. stopper uses a flat diaphragm surface on the internal surface facing the inside of the container which will permit "red spot" formation on that surface. This phenomenon is caused by the development of a conical break in the diaphragm bottom wall upon insertion of a needle. Thus, when the needle is removed, a red spot of blood develops in the break on the internal or bottom surface of the diaphragm. Thus, if a clinician removes the stopper for taking a sample, the bottom surface of the stopper is contaminated and may cause contamination by the clinician touching the bottom surface of the stopper.

E. P. Percarpio, in his U.S. Pat. Nos. 4,301,936; 4,187,952; 4,186,840; 4,136,794; and 4,111,326, teaches a method for reducing the force required to assemble the stopper in the appropriate tube, while achieving, at the same time, a satisfactory sealing characteristic. The patents describe diaphragms in the stoppers disclosed comprised of curved upper and lower surfaces with a constant diaphragm thickness of 0.04–0.09 inches, with the point being to reduce the thickness of the diaphragm and reduce the effort required to insert the needle through the diaphragm into the tube. There is no recognition in these patents of generating a stopper profile so as to eliminate any tensile stress along the stopper/container interface and to develop complete compressive radial stress at the stopper/container interface.

With this invention, by contrast, a three-dimensional, axisymmetrical computer model has been developed for a stopper for use in, for example, a conventional 13 millimeter diameter evacuated tube. A linear Young's modulus of 500 p.s.i. was used together with a poissons ratio of 0.495. The profile generated, allows for a proper configuration of stopper with appropriate upper and lower surface profiles in order to eliminate any tensile stress along the container/stopper interface.

In connection with generating the desired profile, it is necessary prior to generation to develop the appropriate boundary conditions in order to guide the computer generation. For example, it is important to establish fixed nodal locations in order to identify the region generated. Such positions include for example, points along the bottom surface of the upper annular flange of the stopper which are to remain, in a resulting generated stopper, fixed at the mating top surface of a container. These points do not move in the Z axis direction, and thus define boundaries for the desired profile.

Moreover, loading conditions must be selected for the profile. This is done by selecting a desired container and the desired selected stopper. From this, the nodal points along the tapered surface of the stopper profile which are to meet and conform to a container surface are defined. The distance of the movement of these points of the stopper in the Y axis from the position of the points in the stopper prior to insertion, and the position after insertion in the container are determined for selecting boundary and/or displacement conditions. Thus, a model stopper, so-to-speak, is selected which determines boundary and loading conditions in order to obtain the desired profile.

It should be borne in mind that this invention is directed not only to a stopper for use with blood collection tubes and including both evacuated and non-evacuated blood collection tubes, but also this invention is directed to a stopper cap assembly much like that taught and claimed in U.S. Pat. No. 4,465,200 which is hereby incorporated by reference in its entirety. In that patent, an arrangement is provided for reducing to a minimum the exposure of aerosol or blood droplets which may be evident in removing a blood sample from an evacuated tube on the top surface of the assembly. A cap is provided in combination with the stopper of the assembly which is mounted over the resilient rubber stopper of the evacuated tube. The cap includes a top portion which extends over the top of the stopper to define between the top surface of the stopper and the bottom surface of the extended top portion of the cap a space which serves to contain any blood droplets or aerosol generated by needle insertion and withdrawal.

This patent, while teaching an assembly which is effective for protecting against blood droplets or aerosol on the top surface of the assembly, has no effect upon any such collection of blood droplets which may form on the bottom surface of the diaphragm of the elastomer stopper of the assembly. Thus, as discussed above, the invention here includes a generated stopper profile which eliminates "red spot" on the bottom surface of the diaphragm thereof as well as developing continuous compressive radial stress along the entire stopper/container interface.

With the foregoing and additional objects in view, this invention will now be described in more detail, and other objects and advantages thereof will be apparent from the following description, the accompanying drawings, and the appended claims.

DESCRIPTION OF THE DRAWINGS

FIG. 2 is a sectional view of a stopper generated in accordance with this invention;

FIG. 3 is a longitudinal sectional view of the top of a blood sample tube, which may be evacuated, with a composite closure assembly thereon illustrating the invention;

DETAILED DESCRIPTION OF THE INVENTION

Figure 1:
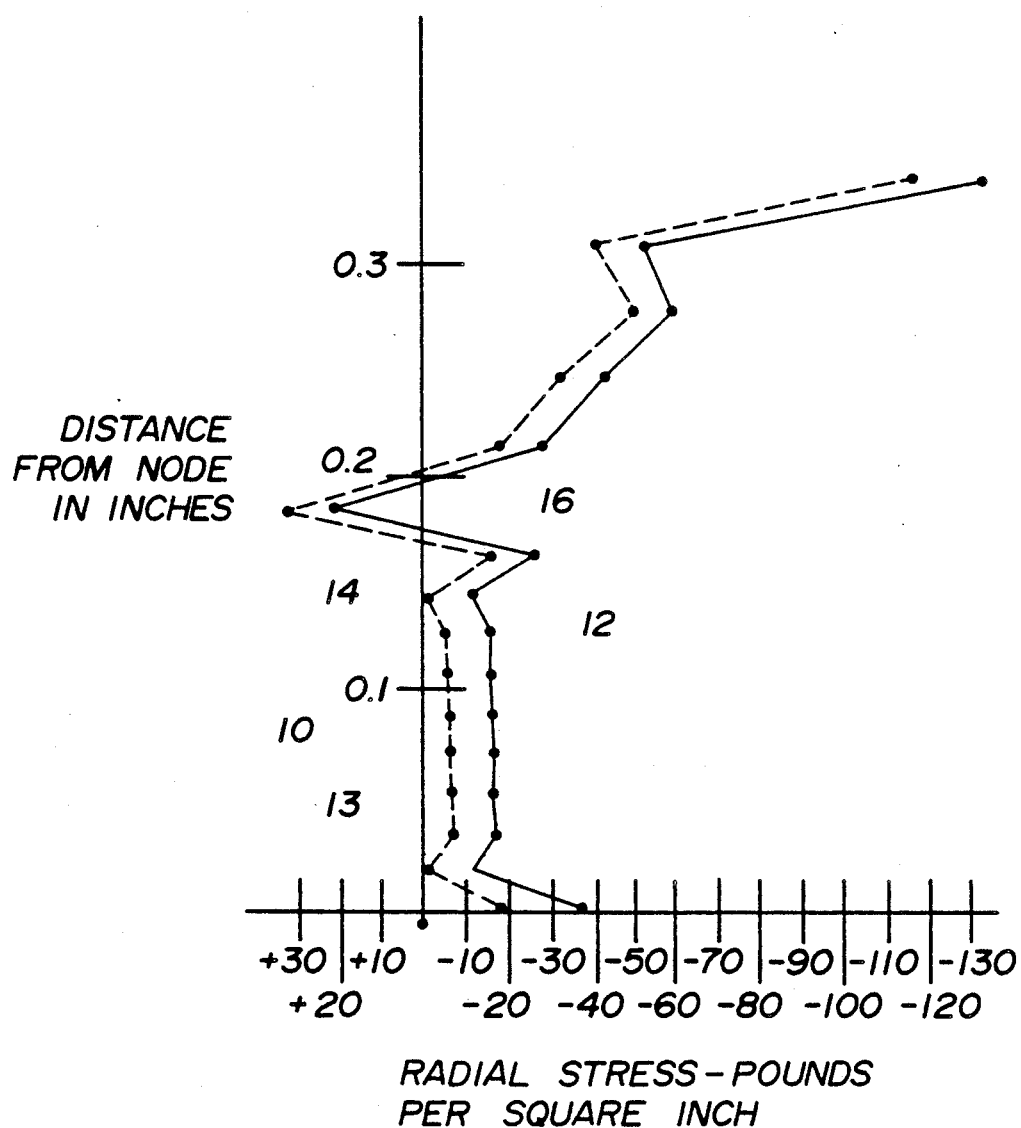
FIG. 1 is a plot of the radial stress distribution at the stopper/tube interface for a conventional 13 millimeter stopper similar to that disclosed in U.S. Pat. No. 4,465,200.

Referring to the drawings in which like reference characters refer to like parts throughout the several views thereof, in FIG. 1, as discussed above, a typical plot of the radial stress distribution at the stopper/tube interface of a conventional 13 millimeter stopper inserted in a conventional blood collection tube having a 13 millimeter internal diameter. In this plot, radial stress is shown in pounds per square inch as the ordinate while the distance from the node 13 is shown in inches as the abscissa. Node 13, as shown, is the innermost contact point between the stopper skirt and the tube wall. Plot 12 is the tube at atmospheric pressure while plot 14 is the tube at evacuated pressure of 26 inches of mercury. As can be seen in FIG. 1, the sealing pressure is negative (i.e., compressive) along the entire stopper/tube interface 10 except for the portion at 0.171–0.204 inches from node 13. This region of tensile stress is known as the "gray band" region in stoppers inserted in tubes of the kind discussed in this application.

FIG. 2 shows a cross-sectional view of a stopper developed in accordance with the invention herein. This stopper when inserted in an appropriate container exhibits no gray bands and has continuous compressive radial stress along the entire stopper/tube interface. Moreover, the stopper has compressive radial stress along the entire inside surface 30 thereof so as to eliminate "red spot" formation on that surface. In FIG. 2, stopper 20 is shown having a radially enlarged upper flange portion 22 and a smaller lower sealing portion 24. Positioned between upper portion 22 and lower portion 24 is a radial notch 26 which accommodates the bead formed on the upper edge of an evacuated tube into which the lower portion 24 of stopper 20 is inserted. Positioned centrally in the top surface 21 of stopper 20 is a finger well 28. The purpose of such a well is to segregate a clinician's finger from the top surface 23 of well 28 where a blood droplet may form during removal of a needle from the stopper 20 for obtaining a blood sample contained in a container in which stopper 20 is inserted.

As can be seen in FIG. 2, the bottom surface 30 of stopper 20 is convex. Because of this general outline of stopper 20, a compressive radial stress is developed along the entire surface 30, as discussed above, and as will be discussed in more detail below.

As purely illustrative of the dimensions of stopper 20, diameter 34 may be, for example, 0.616 inches while notch 26 may have a radius of 0.015. Dimension 36 may be, for example, 0.12 inches while dimension 40 may be 0.275 inches and dimension 42, 0.31 inches.

As a further indication of representative dimensions of the invention, dimension 38 may be 0.125 inches.

As can be seen further in FIG. 2, the surface 32 of the lower portion 24 of stopper 20 may be tapered slightly toward the axis of stopper 20 in a downward direction from radial notch 26 to the bottom edge 27 of the stopper. As further illustrative of dimensions of stopper 20, dimension 44 may be 0.388 inches while dimension 46 may be 0.424 inches and dimension 48 may be 0.434 inches.

As further illustrative of modifications which may be made relative to stopper 20, reference is made to the following Table I which shows slight modifications in the dimensions 44, 46 and 48, as required for various applications of the embodiment of stopper 20 shown in FIG. 2.

TABLE I

| STOPPER | 44 | 46 | 48 |
|---|---|---|---|
| 1 | 0.388 | 0.424 | 0.434 |
| 2 | 0.393 | 0.429 | 0.439 |
| 3 | 0.398 | 0.434 | 0.444 |
| 4 | 0.403 | 0.439 | 0.449 |
| 5 | 0.408 | 0.444 | 0.454 |

FIG. 3 shows a composite stopper cap assembly similar to that disclosed in U.S. Pat. No. 4,465,200, but utilizing the particular configuration of stopper generated in accordance with the invention herein. Thus, as can be seen in FIG. 3, stopper 20 is shown positioned in the top 72 of a blood collection tube 70, of which only the top portion is shown. Tube 70, as will be understood by practitioners-in-the-art, may or may not be evacuated, as required, depending upon the purpose to which it is to be used. As can be seen in FIG. 3, the top of tube 70 includes an annular bead 72 inserted in the radial notch 26 of stopper 20. This has the purpose of maintaining stopper 20 firmly inserted in the top of tube 20 until it is to be removed for removing a sample from tube 70, as required.

Extending over the top of stopper 20 is a plastic cap assembly 74 which may be comprised of a flexible thermoplastic resin, and which includes a radially extending top 75 for extending over the top surface 21 of stopper 20. This radially extending top surface 75 defines an opening 76 through which a needle may pass to be inserted into and through stopper 20. This "overhang" 75 of the plastic cap of the assembly of the invention serves to define a compartment or area 78 for receiving and containing any blood droplets or blood aerosol which may develop during the insertion and removal of needles through stopper 20. Also, the top finger well 28 of stopper 20 serves to enhance this containing function of the assembly shown.

As can be seen in FIG. 3, the bottom surface 30 of stopper 20 may have an annular tapered end edge portion 84 for ease of insertion of the lower portion 24 of stopper 20 into the top of tube 70. Formed on the outer surface of the cap 74 are a plurality of circumferentially spaced ribs 80 which serve to provide a gripping surface for the assembly for removing the assembly from tube 70. In this connection, an integral annular abutment 82 is provided which engages the bottom surface 25 of stopper upper annular flange portion 22 so as to grip and remove stopper 20 when the outer surface of cap 74 is gripped and urged outwardly from the opening of tube 70. Also, annular abutment 82 includes a tapered surface 83 for ease of assembly of the plastic cap 74 over the upper annular flange 22 of stopper 20.

Figure 4:
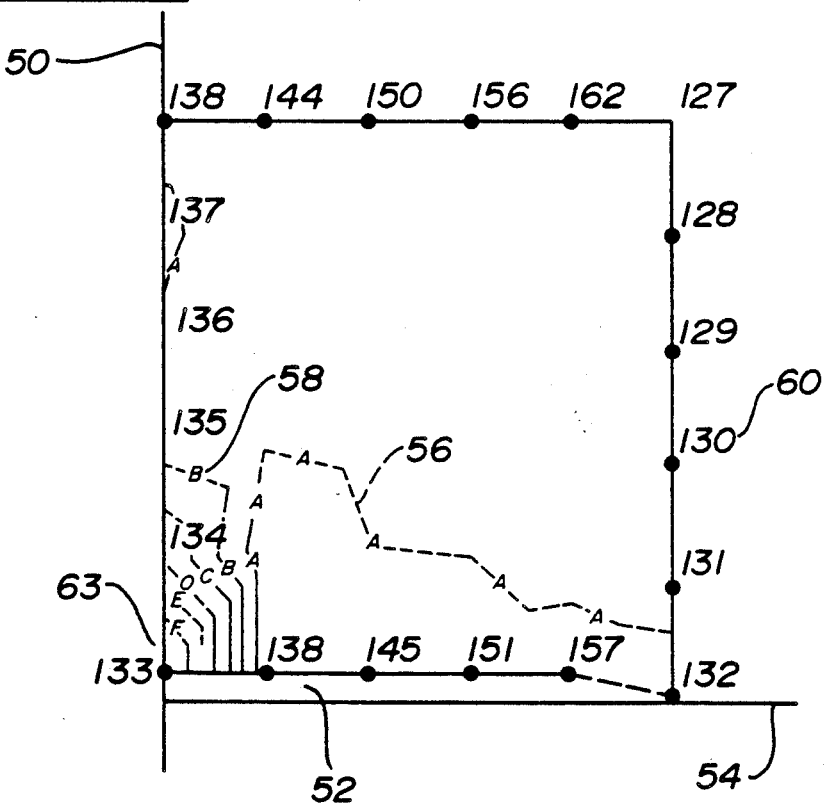
FIG. 4 shows the radial stress distribution at the inside surface of a stopper of the prior art similar to that disclosed in U.S. Pat. No. 4,465,200.
Figure 5:
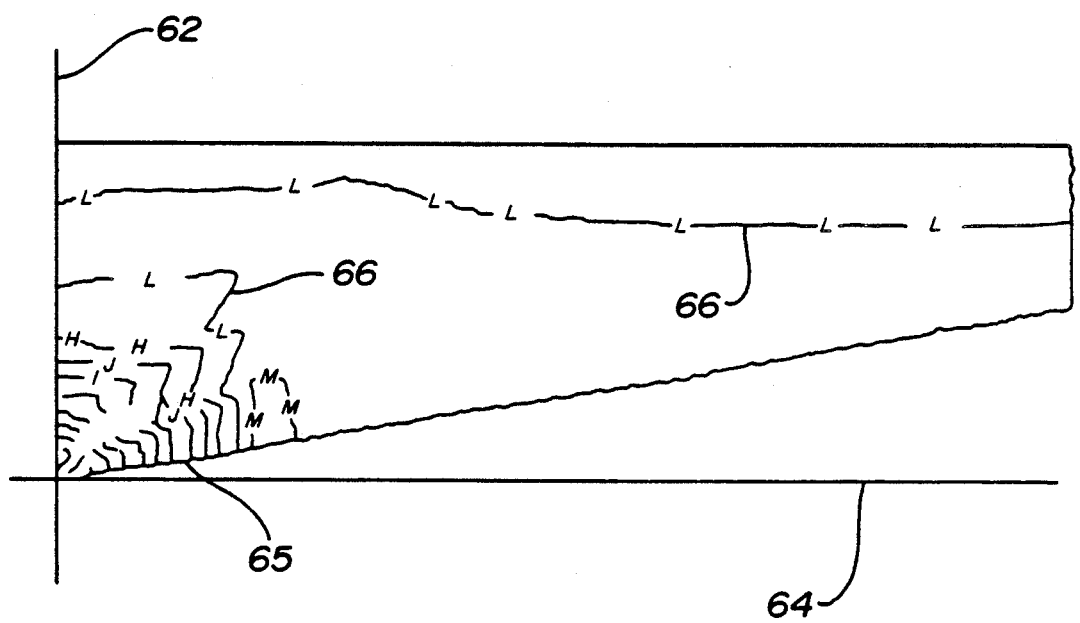
FIG. 5 shows the radial stress distribution at the inside surface of the diaphragm around the center line of a stopper generated according to this invention.

FIG. 4 shows a radial stress contour plot of a prior art stopper, while FIG. 5 is a similar plot of radial stress contours for a stopper illustrating this invention. As both FIGS. 4 and 5 show, radial stress lines such as 56, 58 and 66 are generated around the axes 50, 62, respectively, of the stoppers, and particularly adjacent the inside surfaces 52, 65 of the diaphragm of the stopper. If the stresses are tensile, when a needle is inserted in the diaphragm in the vicinity of axis 50 as in FIG. 4, the continuity of surface 52 is broken and an open cavity 63 is formed. This cavity may be filled with blood when the needle is withdrawn. If the stresses are compressive, no red spot is formed.

Thus, when the stopper is removed from the tube, a red spot of blood is evident at this location and serves as a further potential exposure of contamination to the clinician. As further illustrative of the plot shown in FIG. 4, for example, the line designated A has a value of minus 100 pounds per square inch while the line B is zero and line C is plus 100 pounds per square inch. The numbers in the plot shown in FIGS. 4 and 5 designated as, for example, 131, 138 and 60 are merely nodal locations to identify the region for the user on the figures generated. Lines are drawn through these points to provide a coordinate grid to provide dimensions for the figure generated. The remaining values for FIGS. 4 and 5 are as follows.

| FIG. 4 Values | FIG. 5 |
|---|---|
| A −100 p.s.i. | A −240 p.s.i. |
| B 0 p.s.i. | B −220 p.s.i. |
| C +100 p.s.i. | C −200 p.s.i. |
| D +200 p.s.i. | D −180 p.s.i. |
| E +300 p.s.i. | E −160 p.s.i. |
| F +400 p.s.i. | F −140 p.s.i. |
| G +500 p.s.i. | G −120 p.s.i. |
|  | H −100 p.s.i. |
|  | I −80 p.s.i. |
|  | J −60 p.s.i. |
|  | K −40 p.s.i. |
|  | L −20 p.s.i. |
|  | M p.s.i. |

With respect to FIGS. 4 and 5, FIG. 4 figures are for a 13 millimeter conventional stopper similar to that disclosed in U.S. Pat. No. 4,465,200 with an evacuated 13 millimeter diameter tube. With respect to FIG. 5, an 0.434 inch diameter tube is used with a composite stopper assembly illustrating this invention.

Figure 6:
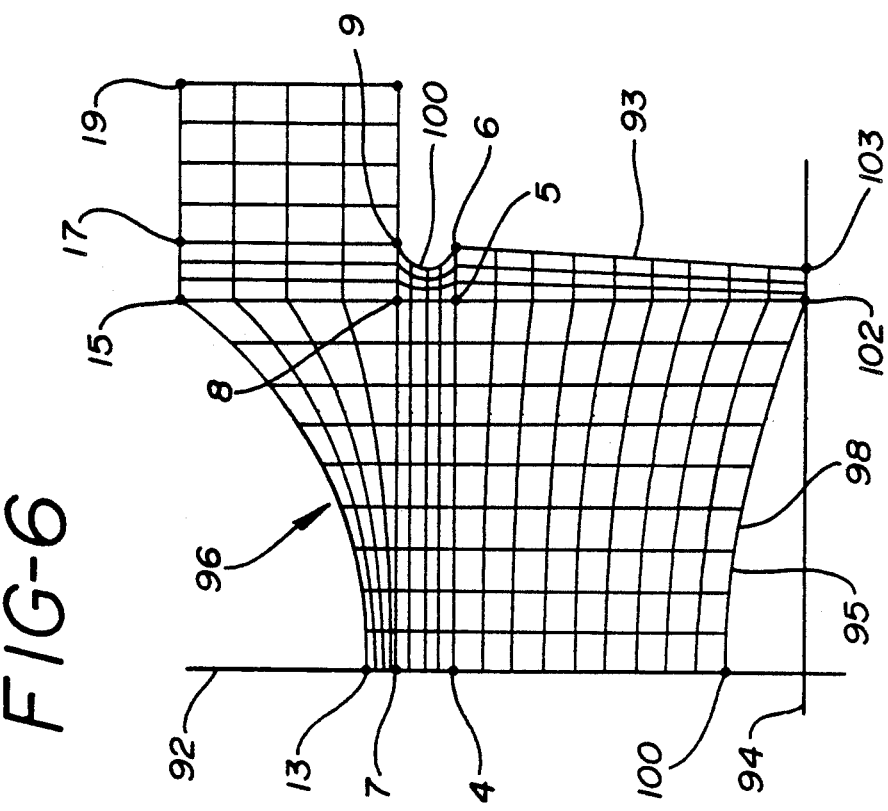
FIG. 6 shows an additional embodiment of computer generated diaphragm design and further illustrating the invention.

FIG. 6 shows a further computer generated stopper design embodiment of this invention. The figure shows the geometry of the design and the nature of the compressive radial stress developed on the stopper/tube interface 93. The analysis shows that the radial surface stresses along the entire 0.49044 inch radius 95 are all compressive including those at the center line of the stopper. In referring to FIG. 6, 94 is the Y axis while 92 is the Z axis. The Z axis 92 represents the axis of the annular stopper design. The points shown in FIG. 6 such as 100, 102 and 103 are distances from the Y and Z axis given in rectangular coordinate format. Thus 100 is zero distance from the Z axis 92, while being 0.04 inches from the Y axis, whereas 102 is 0.194 inches from the Z axis while being at zero inches from the Y axis. As further illustrative of these distances, point 15 is 0.199 inches from the Z axis while being 0.335 inches from the Y axis. Radius 100 is 0.015 inches while radius 96 is 0.23172 inches. As noted above, radius 98 is 0.49044 inches.

Thus, the computer study shown in FIG. 6 indicates that there will be no gray bands in the sealing area and no red spot formation on the inside surface 95 of the diaphragm. The diaphragm of the stopper generated is 0.19 inches thick at the center line which provides good vacuum retention while permitting satisfactory needle penetration. The upper radius 96 provides a slightly different configuration of finger well but which still serves to prevent contact of the surface 96 with the user's finger.

Figure 7:
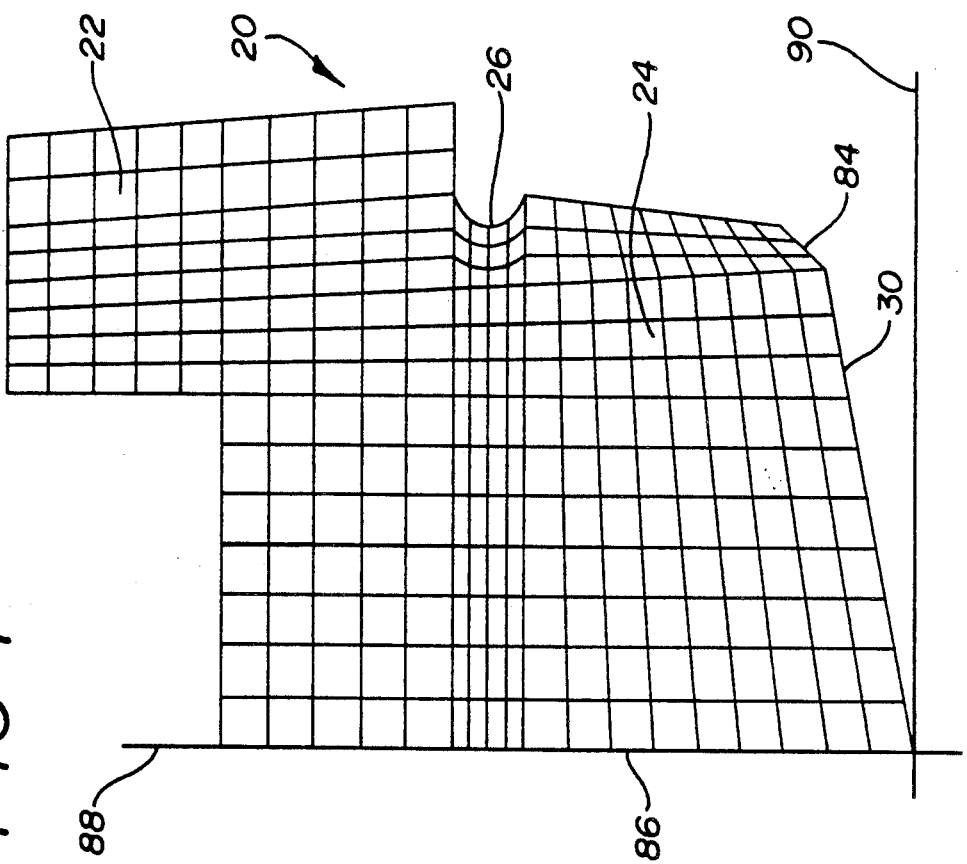
FIG. 7 is a computer generated design similar to that taught and described in FIG. 6 but showing the embodiment of computer generated design of the stopper illustrated in FIG. 2.

As further illustrative of computer plots generated for stopper designs in accordance with the invention herein, one may note the plot shown in FIG. 7 which is the plot of stopper 20 shown in FIG. 3. Thus, stopper 20 has an axis 86 along the Z axis of the configuration with an upper annular portion 22 and a lower portion 24 for insertion in a cooperating tube. The radial notch 26 is, as discussed above, for receiving the top bead of a tube into which the stopper is inserted. Stopper 20 includes the annular tapered edge 84 along the bottom surface 30 thereof for easy insertion of a stopper generated according to the design shown in FIG. 7 into a tube.

Thus, there is provided, in accordance with this invention, a new stopper arrangement for closing containers in which a superior sealing requirement is needed. Also, in accordance with this invention, a new composite closure assembly for blood sample tubes whether evacuated or not is provided. The arrangement of the invention herein is more hygienic to the user and the patient in that lower contamination from blood is obtained from the structure taught and claimed herein. That is, there is lower contamination within the assembly itself reducing exposure of a technician to aerosol around the top edge or blood droplets accumulating on the bottom surface of the stopper. Moreover, and as will be understood by practitioners-in-the-art, there is a substantial reduction in cost in the stopper of the invention herein in that the entire configuration is precisely generated to reduce any excessive use of elastomer materials, which are expensive, while at the same time obtaining the most appropriate sealing characteristics at the closure/container interface.

As is apparent from the foregoing, the arrangements of apparatus provided in accordance herewith are readily and simply manufactured by mass production techniques in conventional molding procedures and the parts may be simply assembled and mounted on containers with a limited amount of effort.

While the device and method of forming the device as herein disclosed form preferred embodiments of this invention, this invention is not limited to these specific devices and methods, and changes can be made therein without departing from the scope of the invention which is defined in the appended claims.

What is claimed is:

1. A method for generating a stopper profile and for generating stoppers from said profile, for sealing containers, from a three-dimensional axisymmetrical computer model, characterized by (a) selecting in a first selecting step an elastomeric material for said profile;
(b) selecting in a second selecting step a linear modulus for said profile;
(c) selecting in a third selecting step a poissons ratio for said profile;
(d) selecting in a fourth selecting step the desired boundary conditions for said profile;
(e) selecting in a fifth selecting step the desired loading conditions for said profile, including selecting the bottom surface of said stopper profile to have continuous compressive stresses along the entire extent thereof upon insertion of the resulting stopper into a container, and selecting the outer surface of the resulting stopper which is to be in engagement with the walls of the container into which it is inserted to have continuous compressive radial stresses along the entire length thereof with the container walls;
(f) using the information from said five recited selecting steps and generating a three-dimensional axisymmetrical computer model for said profile;
(g) utilizing said three-dimensional axisymmetrical computer model from said generating step to generate a stopper profile;
(h) utilizing, in a second generating step, said generated stopper profile for making a stopper mold; and
(i) utilizing in a third generating step, said mold for forming a plurality of stoppers for sealing containers.

2. The method of claim 1, further characterized by
(a) said linear modulus is 500 pounds per square inch.

3. The method of claim 1 further characterized by
(a) said poissons ratio is 0.495.

* * * * *